US012765874B2

(12) United States Patent
Housman et al.

(10) Patent No.: US 12,765,874 B2
(45) Date of Patent: Oct. 20, 2026

(54) SURGICAL FIXATION ASSEMBLIES AND METHODS OF USE

(71) Applicants: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(72) Inventors: Mark Edwin Housman, North Attleboro, MA (US); Benjamin M. Hall, Roslindale, MA (US); Jay A. Shah, Brighton, MA (US); Ian K.Y. Lo, Calgary (CA)

(73) Assignees: SMITH & NEPHEW, INC., Memphis, TN (US); SMITH & NEPHEW ORTHOPAEDICS AG, Zug (CH); 3)SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 31 days.

(21) Appl. No.: 19/108,782

(22) PCT Filed: Sep. 20, 2023

(86) PCT No.: PCT/US2023/033259
§ 371 (c)(1),
(2) Date: Mar. 5, 2025

(87) PCT Pub. No.: WO2024/072678
PCT Pub. Date: Apr. 4, 2024

(65) Prior Publication Data
US 2026/0076665 A1 Mar. 19, 2026

Related U.S. Application Data

(60) Provisional application No. 63/409,956, filed on Sep. 26, 2022.

(51) Int. Cl.
*A61B 17/04* (2006.01)

(52) U.S. Cl.
CPC .... *A61B 17/0401* (2013.01); *A61B 2017/044* (2013.01)

(58) Field of Classification Search
CPC ............ A61B 17/0401; A61B 17/0485; A61B 17/06166; A61B 2017/0409;
(Continued)

(56) References Cited

U.S. PATENT DOCUMENTS 8,821,541 B2 * 9/2014 Dreyfuss ............ A61B 17/0401 606/232
9,775,702 B2 10/2017 Arai et al.
(Continued)

FOREIGN PATENT DOCUMENTS

WO 2021225858 A1 11/2021

*Primary Examiner* — Phong Son H Dang
(74) *Attorney, Agent, or Firm* — ArentFox Schiff LLP; Joseph M. Maraia

(57) ABSTRACT

Surgical fixation assemblies include a screw-in anchor with a suture construct attached to and extending through an interior of the anchor. The suture construct has two finger trap splices to trap suture that has been passed through them when the construct is placed in tension. Transfer sutures containing loops are preloaded through the finger trap splices and used to pull the ends of the repair sutures through the finger trap splices to form reducing loops around or through captured tissue.

20 Claims, 9 Drawing Sheets

(58) Field of Classification Search
CPC ....... A61B 2017/044; A61B 2017/0445; A61F 2/0811; A61F 2002/0852
See application file for complete search history.

(56) References Cited

U.S. PATENT DOCUMENTS

| | | | | |
|---|---|---|---|---|
| 11,344,290 | B1 * | 5/2022 | Ninh | A61B 17/0401 |
| 2011/0098727 | A1 * | 4/2011 | Kaiser | A61B 17/0401 606/228 |
| 2012/0179199 | A1 | 7/2012 | Hernandez et al. | |
| 2014/0277129 | A1 * | 9/2014 | Arai | A61B 17/0401 606/232 |
| 2014/0277130 | A1 * | 9/2014 | Housman | A61B 17/8877 606/232 |
| 2014/0277192 | A1 * | 9/2014 | Housman | A61B 17/8625 606/104 |
| 2016/0270777 | A1 * | 9/2016 | Miller | A61B 17/0401 |
| 2017/0049432 | A1 * | 2/2017 | Dooney, Jr. | A61B 17/0487 |
| 2017/0049434 | A1 * | 2/2017 | Dooney, Jr. | A61B 17/0401 |
| 2017/0105716 | A1 | 4/2017 | Burkhart | |
| 2017/0189007 | A1 * | 7/2017 | Burkhart | A61B 17/0401 |
| 2022/0175514 | A1 * | 6/2022 | Verma | A61F 2/0811 |
| 2024/0197314 | A1 * | 6/2024 | Bachmaier | A61B 17/0401 |
| 2025/0312075 | A1 * | 10/2025 | Crook | A61B 17/842 |

* cited by examiner

SURGICAL FIXATION ASSEMBLIES AND METHODS OF USE

CROSS-REFERENCE TO RELATED APPLICATIONS

This application is the U.S. national phase entry under 35 U.S.C. § 371 of International Application No. PCT/US2023/033259, filed Sep. 20, 2023, entitled SURGICAL FIXATION ASSEMBLIES AND METHODS OF USE, which in turn claims priority to and benefit of U.S. Provisional Application No. 63/409,956, filed Sep. 26, 2022, the contents of which are incorporated herein by reference in their entirety for all purposes.

FIELD

The present disclosure relates to surgical repair of tissue and, more specifically, to devices and methods for inserting a suture anchor used in such repair.

BACKGROUND

During a joint repair, surgeons commonly use suture anchors to attach a soft tissue graft to bone. Typically, a surgeon uses an inserter tool to implant a suture anchor into a drilled hole in bone. The surgeon then connects one or more sutures or suture tape to the suture anchor. The surgeon passes the suture around or through tissue and subsequently ties a knot in the suture to secure the tissue to the bone. However, surgeons often prefer a knotless suture repair that avoids having a knot interfere with the repair.

SUMMARY

Surgical fixation assemblies described herein include a screw-in anchor with a suture construct attached to and extending through an interior of the anchor. The suture construct has two finger trap splices to trap suture that has been passed through them when the construct is placed in tension. Transfer sutures containing loops are preloaded through the finger trap splices and used to pull the ends of the repair sutures through the finger trap splices to form reducing loops around or through captured tissue. Advantageously, this allows for surgeons to complete the repair without tying knots in the suture.

Further examples of the surgical fixation assemblies and methods of this disclosure may include one or more of the following, in any suitable combination.

Examples of a surgical fixation assembly of this disclosure include an anchor having a proximal end, a distal end, and threads extending in an open helical form from the proximal to the distal end. At least one rib extends through an interior of the anchor. A suture bridge extends at least partially through the interior of the anchor. The assembly also includes a suture construct including repair suture having a first repair leg and a second repair leg. A first transfer suture couples to the first repair leg via a first constriction element. A first end of the first transfer suture is a first free end, and a second end of the first transfer suture includes a first transfer loop. A second transfer suture couples to the second repair leg via a second constriction element. A first end of the second transfer suture is a second free end and a second end of the second transfer suture includes a second transfer loop. The suture construct is coupled to the suture bridge such that the first repair leg, the second repair leg, the first transfer suture and the second transfer suture extend through the interior of the anchor.

In further examples, a distal end of the suture bridge has a concave shape. In examples, the at least one rib is two ribs, and the suture bridge is connected to and extends between the two ribs. In examples, the first transfer loop is configured to pull an end of the first repair leg through the first constriction element to form a first reducible loop. In examples, the first constriction element is configured to allow the first reducible loop to be tightened but not loosened. In examples, the second transfer loop is configured to pull an end of the second repair leg through the second constriction element to form a second reducible loop. In examples, the second constriction element is configured to allow the second reducible loop to be tightened but not loosened. In examples, the suture construct is coupled to the suture bridge by a coupling region of the repair leg, the coupling region extending between the first repair leg and the second repair leg. In examples, the first and second constriction elements are adjacent the coupling region. In examples, the coupling region is attached to the suture bridge by one of a luggage tag coupling or a knot. In examples, the anchor is disposed on a distal end of a delivery device such that the first and second repair legs and the first and second transfer sutures extend through a cannulation of the delivery device. In examples, the suture bridge is housed within a slot and the at least one rib is housed within at least one corresponding groove of the delivery device.

Examples of a method of tissue repair of this disclosure include inserting an anchor of a surgical fixation assembly into a first tissue. The surgical fixation assembly includes the anchor having a proximal end, a distal end, and threads extending in an open helical form from the proximal to the distal end. At least one rib extends through an interior of the anchor. A suture bridge extends at least partially through the interior of the anchor. The surgical fixation assembly also includes a suture construct including a repair suture having a first repair leg and a second repair leg. A first transfer suture couples to the first repair leg via a first constriction element. A first end of the first transfer suture is a first free end and a second end of the first transfer suture includes a first transfer loop. A second transfer suture couples to the second repair leg via a second constriction element. A first end of the second transfer suture is a second free end and a second end of the second transfer suture includes a second transfer loop. The method also includes passing the first repair end around or through a second tissue and through the first transfer loop. The method also includes, using the first free end of the first transfer suture, pulling the first repair end through the first constriction element to form a first reducible loop around or through the second tissue. The first constriction element is configured to allow the first reducible loop to be tightened but not loosened around or through the second tissue.

In further examples, the method also includes passing the second repair end around or through a third tissue and through the second transfer loop. The method also includes, using the first free end of the second transfer suture, pulling the second repair end through the second constriction element to form a second reducible loop around or through the third tissue. The second constriction element is configured to allow the second reducible loop to be tightened but not loosened around or through the third tissue. In examples, the method also includes inserting the anchor into the first tissue with a delivery device. The anchor is disposed on a distal end of the delivery device such that the first and second repair legs and the first and second transfer sutures extend through a cannulation of the delivery device. In examples, the method also includes attaching a coupling region of the repair leg to the suture bridge. The coupling region extends between the first repair leg and the second repair leg. In examples, the first tissue is bone. In examples, the second tissue is a soft tissue graft.

A reading of the following detailed description and a review of the associated drawings will make apparent the advantages of these and other features. Both the foregoing general description and the following detailed description serve as an explanation only and do not restrict aspects of the disclosure as claimed.

BRIEF DESCRIPTION OF THE DRAWINGS

Reference to the detailed description, combined with the following figures, will make the disclosure more fully understood, wherein.

DETAILED DESCRIPTION

Figure 1:
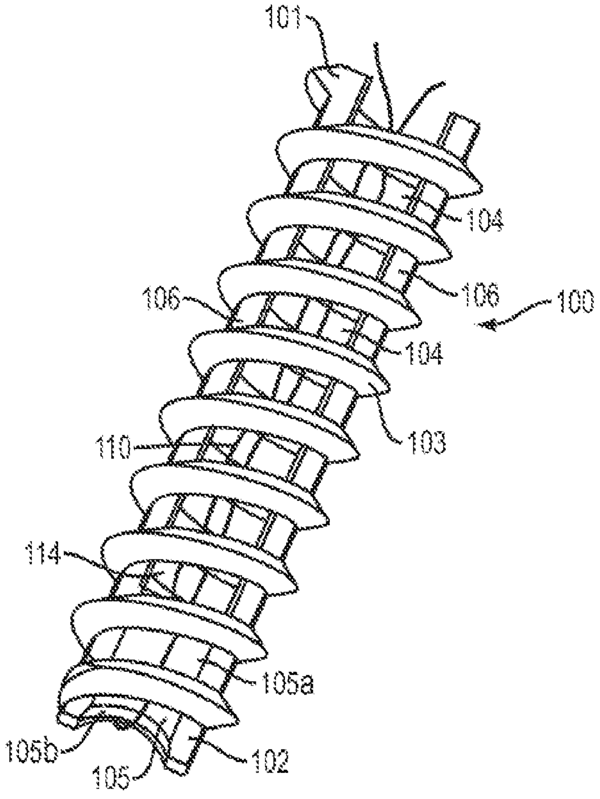
FIG. 1 (PRIOR ART)
FIG. 1 illustrates an example of an anchor for use with the surgical fixation assembly of this disclosure.

In the following description, like components have the same reference numerals, regardless of different illustrated examples. To illustrate examples clearly and concisely, the drawings may not necessarily reflect appropriate scale and may have certain features shown in somewhat schematic form. The disclosure may describe and/or illustrate features in one example, and in the same way or in a similar way in one or more other examples, and/or combined with or instead of the features of the other examples.

In the specification and claims, for the purposes of describing and defining the invention, the terms "about" and "substantially" represent the inherent degree of uncertainty attributed to any quantitative comparison, value, measurement, or other representation. The terms "about" and "substantially" moreover represent the degree by which a quantitative representation may vary from a stated reference without resulting in a change in the basic function of the subject matter at issue. Open-ended terms, such as "comprise," "include," and/or plural forms of each, include the listed parts and can include additional parts not listed, while terms such as "and/or" include one or more of the listed parts and combinations of the listed parts.

FIG. 1 illustrates an example of an anchor 100 for use with the surgical fixation assembly 10 of this disclosure. As shown in FIG. 1, the anchor 100 may include a proximal end 101 and a distal end 102. A majority of the anchor 100 may include screw threads 103 in the form of an open helical coil (i.e., a connected series of continuous, regularly spaced turns extending in a helical or spiral form) extending substantially from the proximal end 101 to the distal end 102 with apertures 104 being defined by the spaces between the turns of the coil. The open helical coil may define an internal volume 114 communicating with the region exterior to the open helical coil through the apertures 104 between the turns of the open helical coil. The distal end 102 may also include a suture bridge 105 that extends a partial length of the anchor 100. The suture bridge 105 may include a proximal end 105*a* and a distal end 105*b*. In examples, the distal end 105*b* may have a concave shape. However, the disclosure also contemplates other suitable shapes of the distal end 105*b*, such as flat, convex, or bulbous. The anchor 100 is configured such that a flexible member 110, such as a suture, can be housed within the anchor 100 with the suture 110 extending around the distal end 105*b* of the suture bridge 105. Additionally, at least one rib 106 may extend through the internal volume 114 along the interior of the screw threads 103. For the purposes of this disclosure, two ribs 106 extend through the internal volume 114. However, the disclosure contemplates more or fewer than two ribs 106. U.S. Pat. No. 9,949,820 to Smith & Nephew, Inc. (Memphis, TN), incorporated herein by reference, shows and describes other non-limiting examples of anchors 100 configured for use with the surgical fixation assembly 10 of this disclosure.

Figure 2:
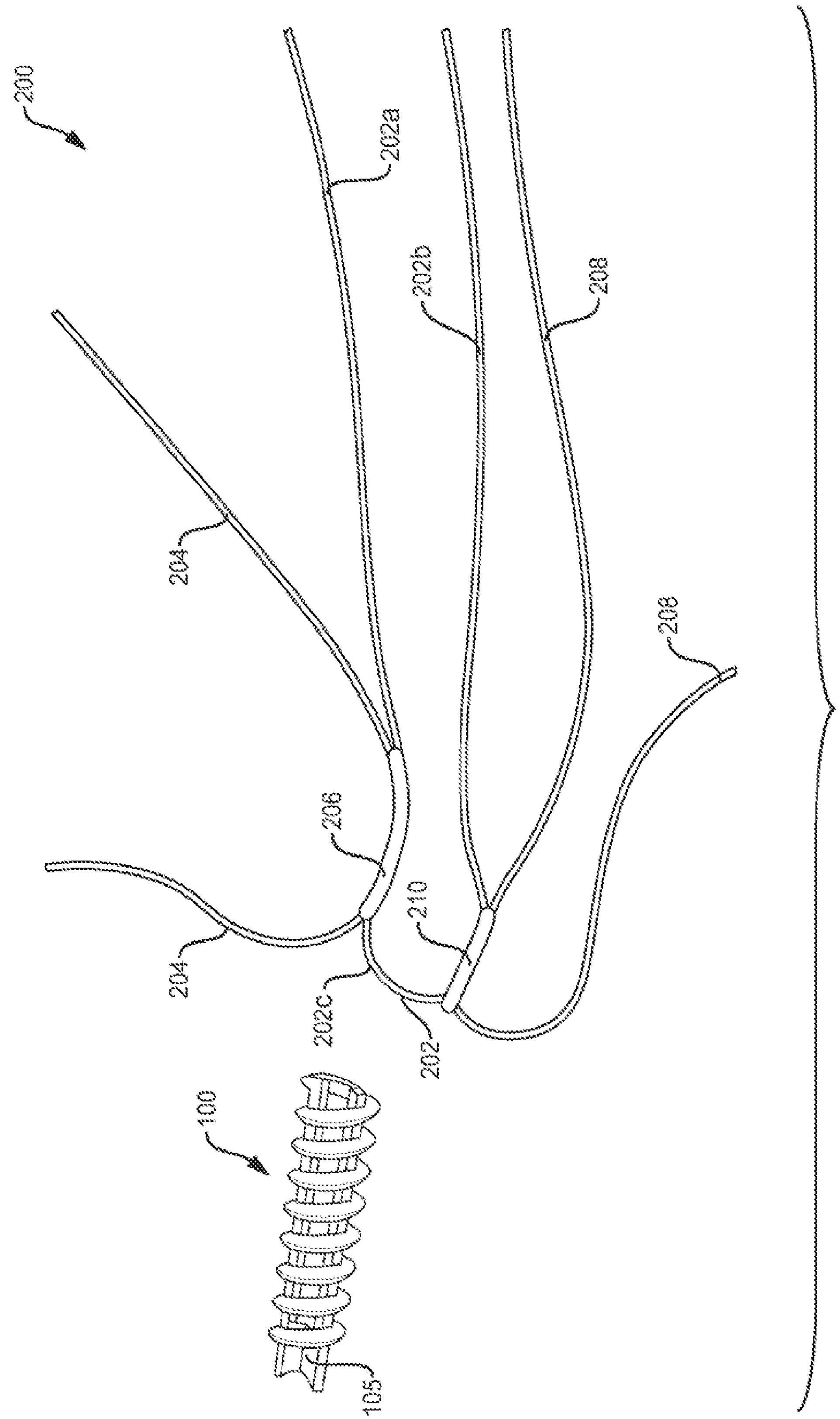
FIG. 2 illustrates an example of the surgical fixation assembly of this disclosure in a disassembled state.

FIG. 2 illustrates an example of the surgical fixation assembly 10 of this disclosure in a disassembled state. As shown in FIG. 2, the surgical fixation assembly 10 may generally comprises an anchor, such as the anchor 100 of FIG. 1, and a suture construct 200 attachable to the anchor 100. The suture construct 200 may include a repair suture 202 having a first repair leg 202*a* and a second repair leg 202*b*. A coupling region 202*c* extends between the first repair leg 202*a* and the second repair leg 202*b* and is configured to attach to the suture bridge 105, as further described below. The first repair leg 202*a* may couple to a first transfer suture 204 via a first constriction element 206 located adjacent the coupling region 202*c*. In examples, the first constriction element 206 may comprise a spliced section that operates in the manner of a "finger trap." Similarly, the second repair leg 202*b* may couple to a second transfer suture 208 via a second constriction element 210 located adjacent the coupling region 202*c* and operating in a similar manner to the first constriction element 206.

Figure 3:
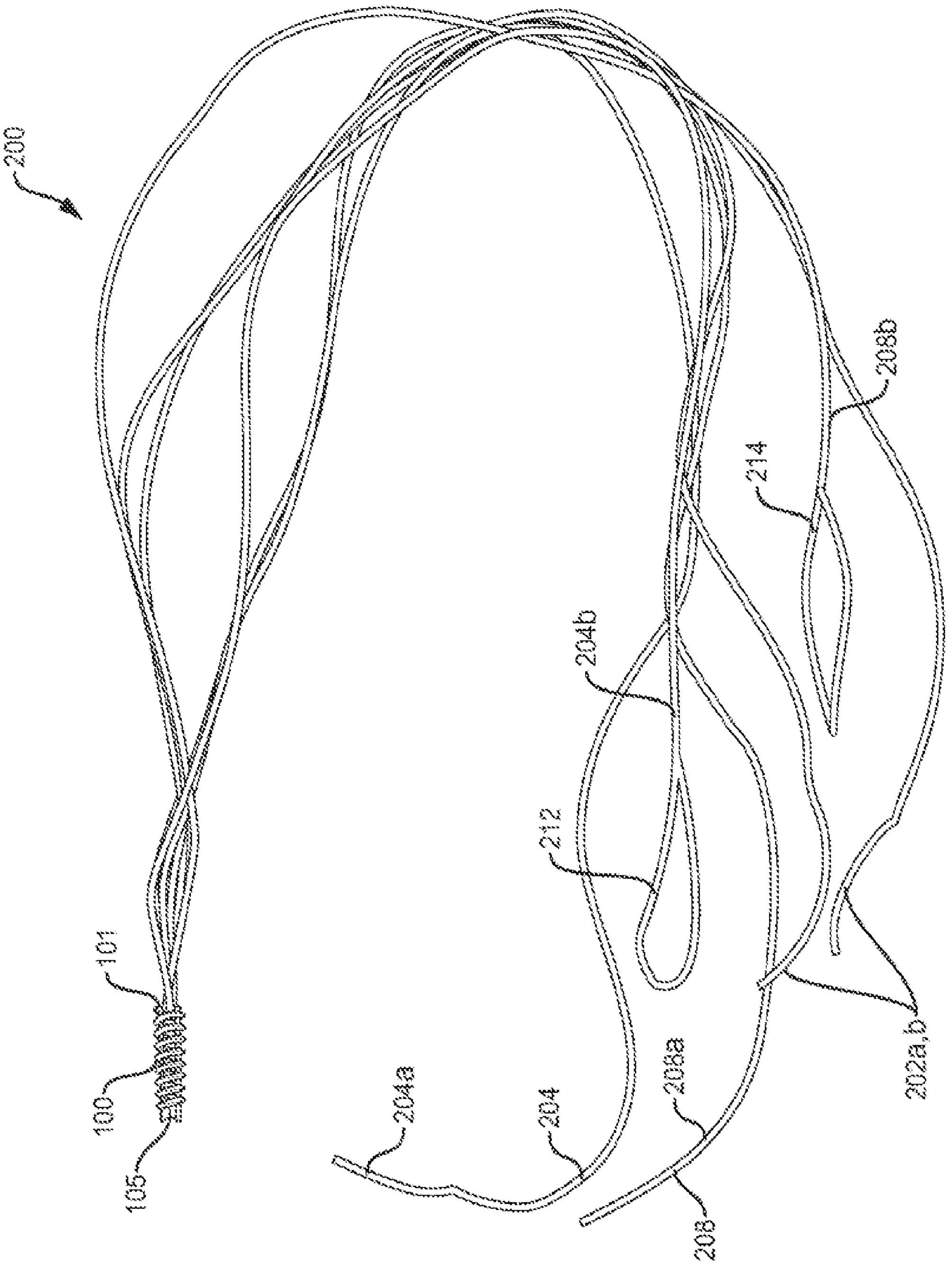
FIG. 3 illustrates an example of the suture construct of this disclosure assembled to the anchor.

FIG. 3 illustrates an example of the suture construct 200 of this disclosure attached to the suture bridge 105 of the anchor 100. As shown in FIG. 3, when the suture construct 200 attaches to the suture bridge 105, the first and second constriction elements 206, 210 may reside within the internal volume 114 of the anchor 100 while the first and second repair legs 202*a,b* and the first and second transfer sutures 204, 208 extend from the proximal end 101 of the anchor 100. A first transfer end 204*a* of the first transfer suture 204 may comprise a first free end and a second transfer end 204*b* of the first transfer suture 204 may comprise a first transfer loop 212. Similarly, a first transfer end 208*a* of the second transfer suture 208 may comprise a second free end and a second transfer end 208*b* of the second transfer suture 208 may comprise a second transfer loop 214, the use of which will be further described below.

Figure 4A:
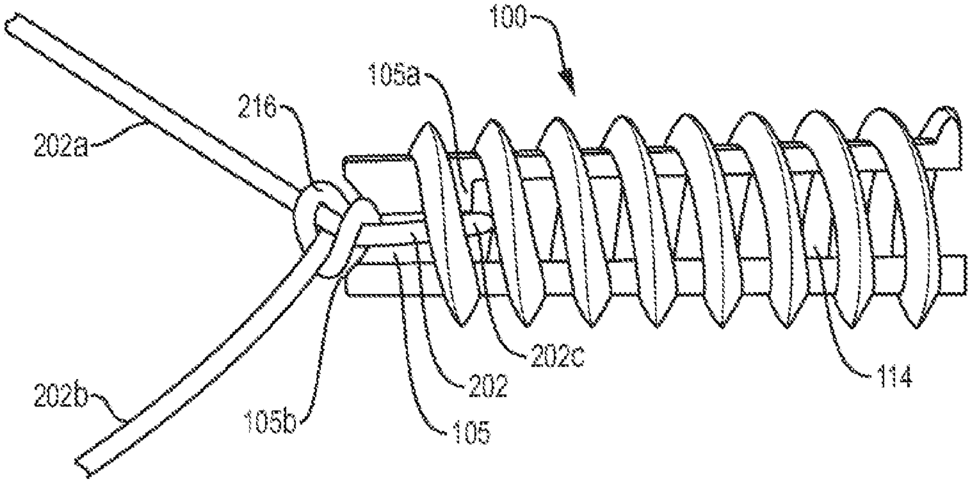
FIGS. 4A and 4B illustrate examples of methods of coupling the repair suture to the anchor.
Figure 4B:
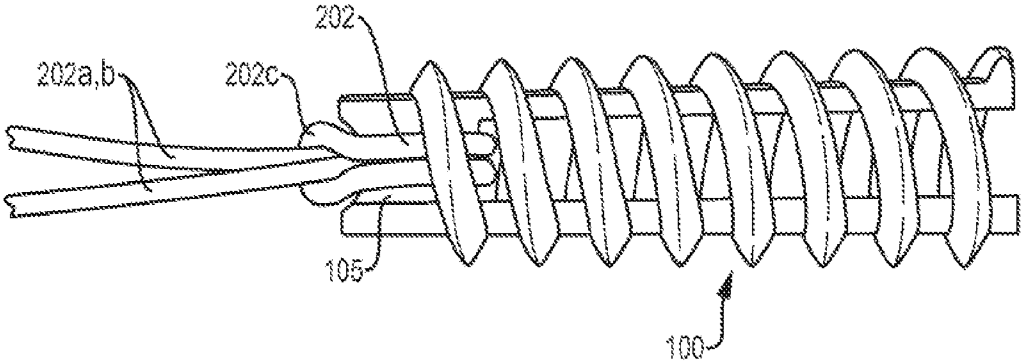

FIGS. 4A and 4B illustrate examples of methods for attaching the repair suture 202 to the suture bridge 105 of the anchor 100. For ease of illustration, FIGS. 4A and 4B show the repair legs 202*a,b* extending distally from the suture bridge 105. However, during normal operation, the repair legs 202*a,b* would instead extend proximally from the suture bridge 105 and through the interior volume 114 of the anchor 100. In the example of FIG. 4A, the coupling region 202*c* may extend around the suture bridge 105 and a knot 216 of any type known in the art may be formed by the repair legs 202*a,b* within the interior volume 114 of the anchor 100. In an alternative example, shown in FIG. 4B, the repair legs 202*a,b* may pass between the coupling region 202*c* and the suture bridge 105 in a "luggage tag" fashion. The disclosure also contemplates any other suitable method that rigidly connects the repair suture 202 to the anchor 100, such as overmolding, ultrasonic welding or adhesives.

Figure 5A:
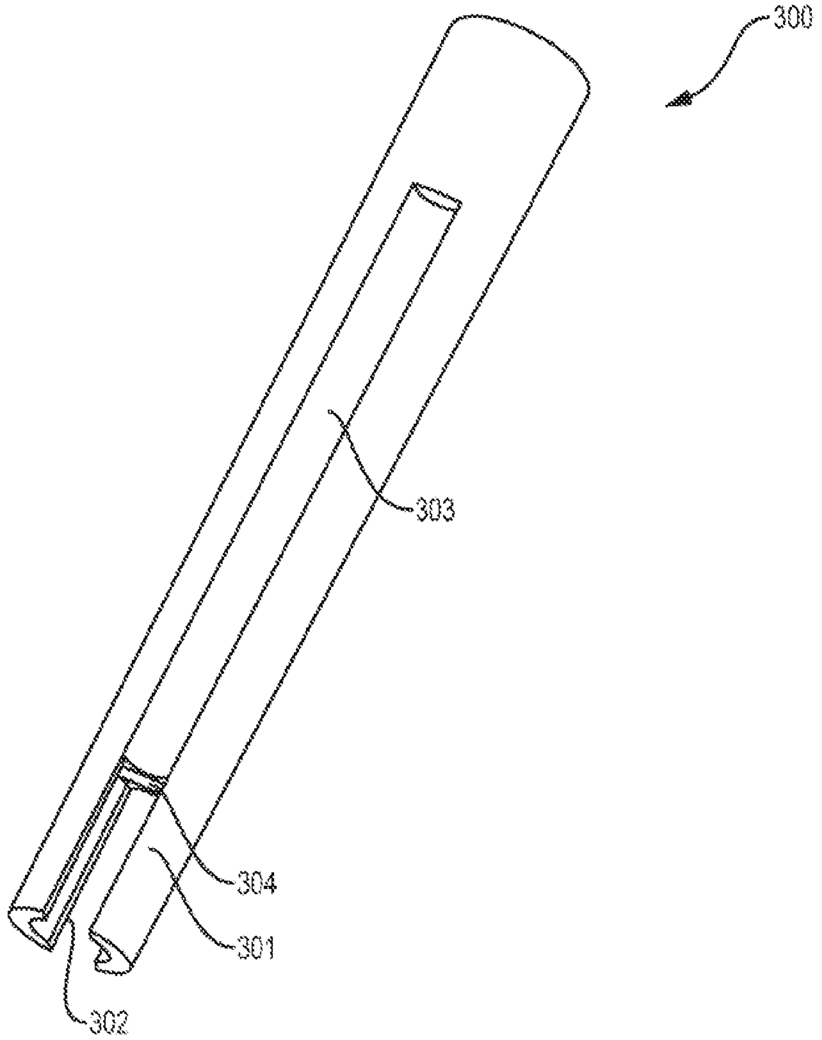
FIG. 5A (PRIOR ART)
FIG. 5A shows an example of a delivery device for delivering the surgical fixation assembly of this disclosure to a repair site.
Figure 5B:
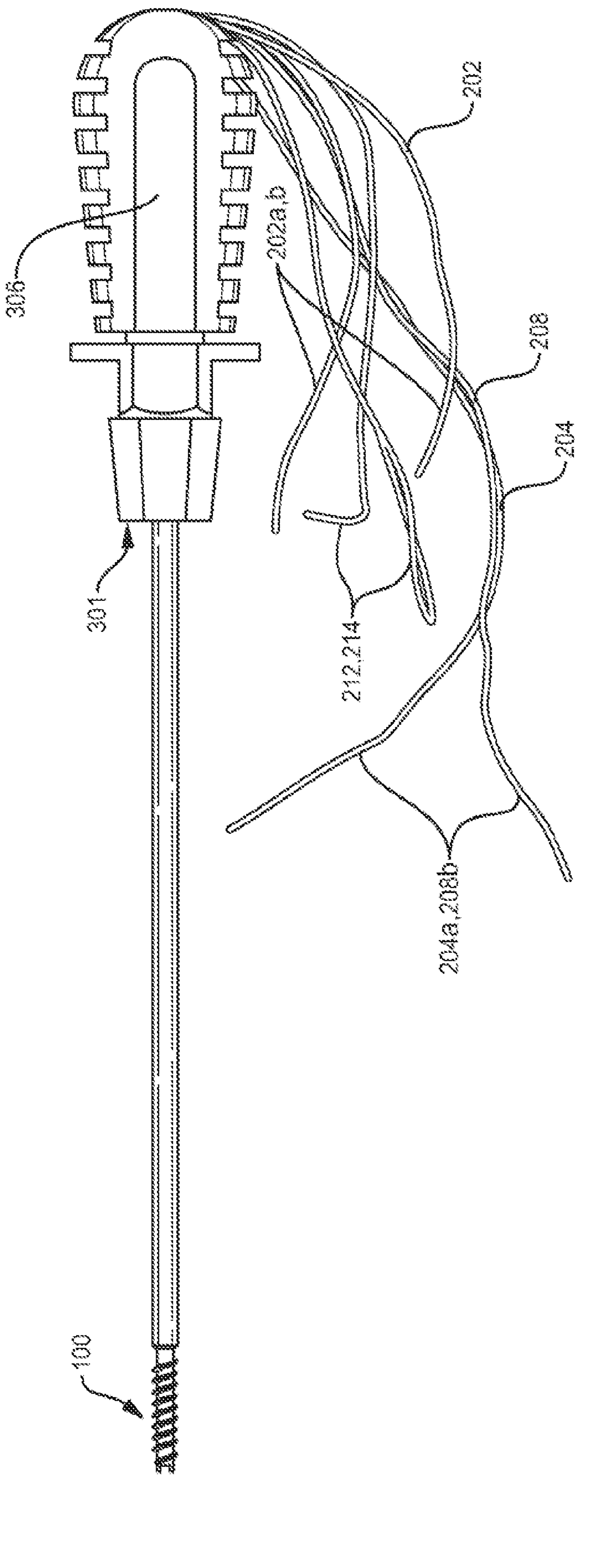
FIG. 5B shows an example of the anchor located on the distal end of the delivery device.

FIG. 5A shows an example of a delivery device 300 for delivering the surgical fixation assembly 10 of this disclosure to a repair site. For clarity purposes, FIG. 5A only shows the distal end 301 of the delivery device 300. However, the delivery device 300 would include a proximal end which may be coupled to a handle assembly 306 (FIG. 5B). The distal end 301 may have a slot 302 and at least one groove 303 extending from the slot 302. A cannulation 304 may extend through the delivery device 300. In use, the anchor 100 may be located on the distal end 301 of the delivery device 300 such that the suture bridge 105 is housed within the slot 302 and the ribs 106 are housed within the grooves 303. U.S. Pat. No. 9,949,820 to Smith & Nephew, Inc. (Memphis, TN), incorporated herein by reference, shows and describes other non-limiting examples of delivery devices 300 configured for use with the surgical fixation assembly 10 of this disclosure.

FIG. 5B shows an example of the anchor 100 located on the distal end 301 of the delivery device 300. As shown in FIG. 5B, when the anchor 100 is located on the delivery device 300, the repair legs 202*a,b*, the transfer ends 204*a*, 208*a*, and the first and second transfer loops 212, 214 extend through the cannulation 304 (FIG. 5A) of delivery device 300 and exit a proximal end of the handle assembly 306. Examples of the repair suture 202 and the transfer sutures 204, 208 can have different coloring to allow the user to differentiate between the two types of sutures.

Figure 6A:
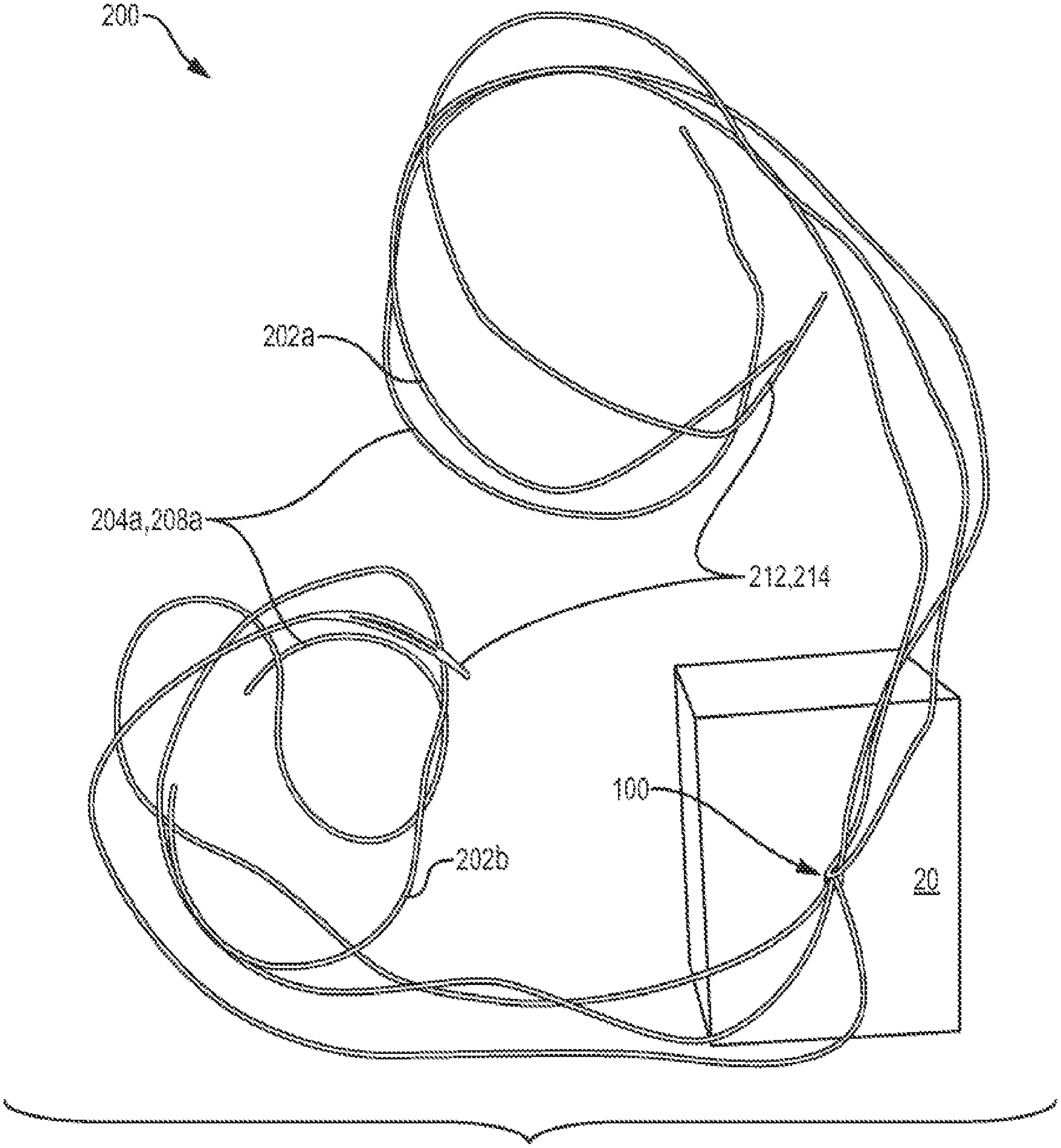
FIGS. 6A-C illustrate an example of a method of using the surgical fixation assembly of this disclosure in a surgical repair.
Figure 6B:
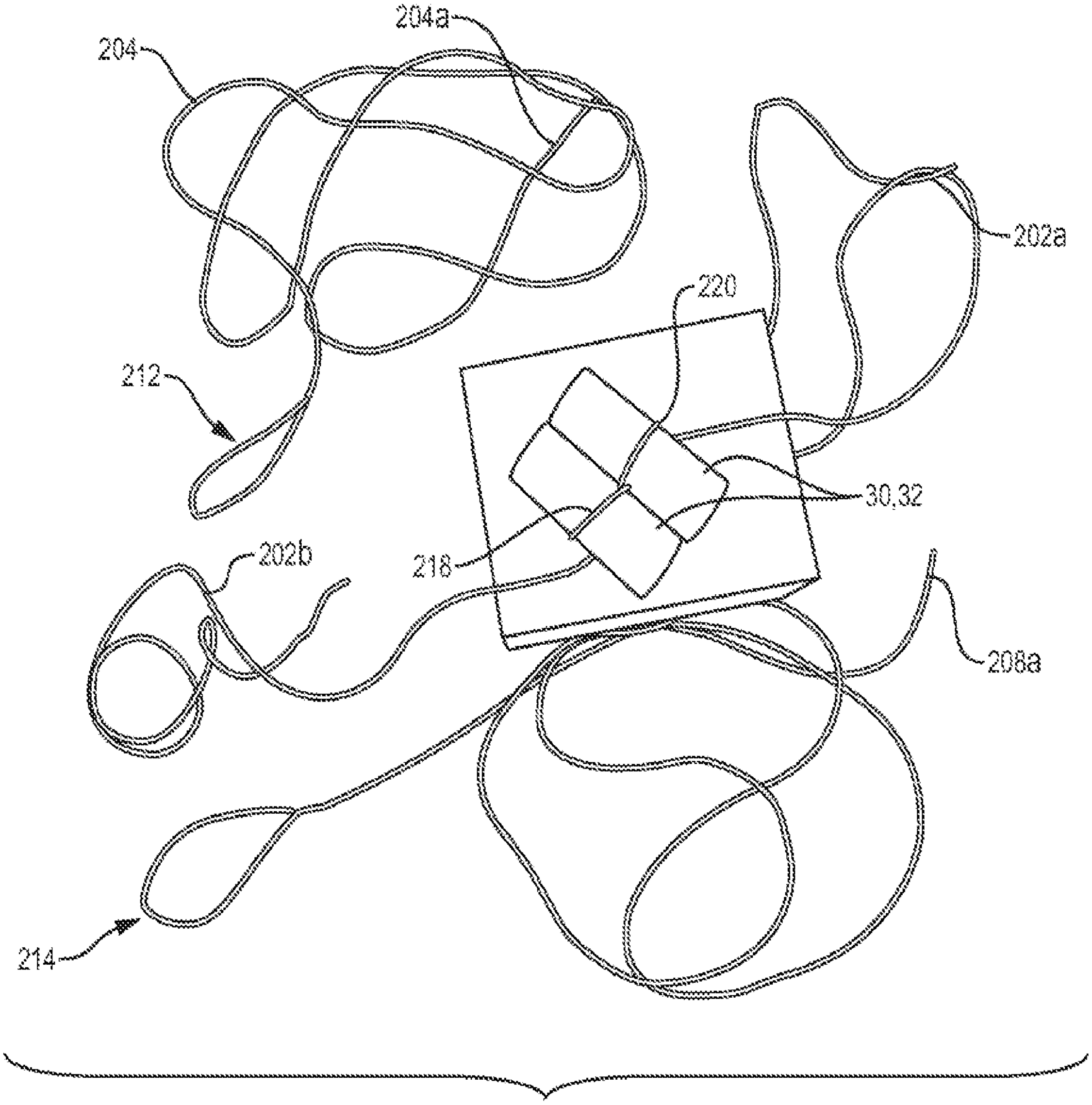
Figure 6C:
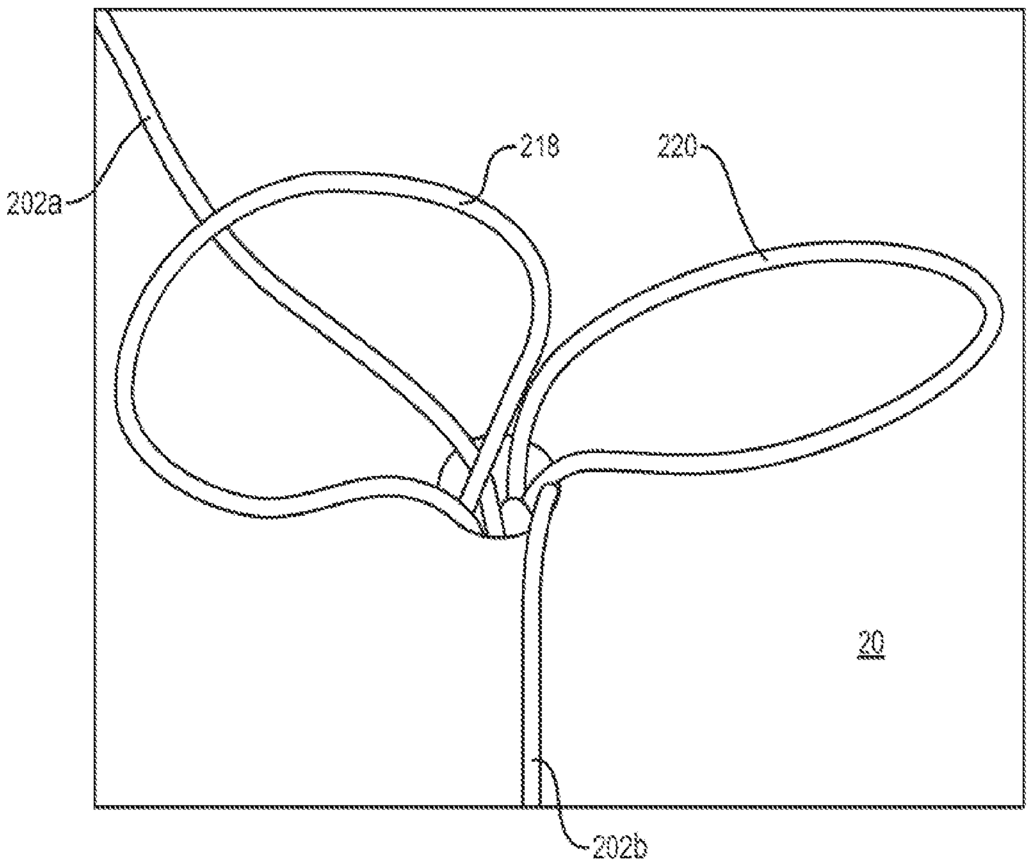

FIGS. 6A-C illustrate an example of a method of using the surgical fixation assembly 10 of this disclosure. As shown in FIG. 6A, a user may rotate the handle assembly 306 to screw the anchor 100 into tissue 20, such as bone. Once the anchor 100 has been fully inserted, the user may then decouple the delivery device 300 from the anchor 100 by pulling the delivery device 300 in a proximal direction, leaving the anchor 100 and the suture construct 200 embedded in the tissue 20. A user may pass the first repair leg 202*a* through the first transfer loop 212 and use the transfer end 204*a* to pull the first repair leg 202*a* through the first constriction element 206, such that the first repair leg 202*a* forms a first reducible loop. Similarly, a user may pass the second repair leg 202*b* through the second transfer loop 214 and use the transfer end 208*a* to pull the second repair leg 202*b* through the second constriction element 210, such that the second repair leg 202*b* forms a second reducible loop. As shown in FIG. 6B, the reducible loops 218, 220 may extend around or through tissue, such as soft tissue grafts 30, 32. The transfer end 204*a* may pull the first transfer loop 212 completely through the first constriction element 206 so that the first transfer suture 204 can be removed from the repair, as shown. Similarly, the transfer end 208*a* may pull the second transfer loop 214 completely through the second constriction element 210 so that the second transfer suture 208 can be removed from the repair. This leaves only the reducible loops 218, 220 and the repair suture ends 202*a,b* extending from the anchor 100. FIG. 6C shows a detailed view of the reducible loops 218, 220 and repair suture ends 202*a,b* with the tissue grafts 30, 32 removed for ease of illustration. Once the reducible loops 218, 220 have been fully tensioned around or through tissue, the constriction elements 206, 210 prevent the reducible loops 218, 220 from loosening, advantageously forming a knotless tissue attachment to bone 20. As a final step, a user may trim the repair suture ends 202*a,b* from the repair.

While the disclosure particularly shows and describes preferred examples, those skilled in the art will understand that various changes in form and details may exist without departing from the spirit and scope of the present application as defined by the appended claims. The scope of this present application intends to cover such variations. As such, the foregoing description of examples of the present application does not intend to limit the full scope conveyed by the appended claims.

The invention claimed is:

1. A surgical fixation assembly comprising:

an anchor comprising:

a proximal end, a distal end, and threads extending in an open helical form from the proximal to the distal end;

at least one rib extending through an interior of the anchor; and a suture bridge extending at least partially through the interior of the anchor; and a suture construct comprising:

a repair suture having a first repair leg and a second repair leg;

a first transfer suture coupled to the first repair leg via a first constriction element, a first end of the first transfer suture comprising a first free end and a second end of the first transfer suture comprising a first transfer loop; and a second transfer suture coupled to the second repair leg via a second constriction element, a first end of the second transfer suture comprising a second free end and a second end of the second transfer suture comprising a second transfer loop;

wherein the suture construct is coupled to the suture bridge such that the first repair leg, the second repair leg, the first transfer suture and the second transfer suture extend through the interior of the anchor.

2. The surgical fixation assembly of claim 1, wherein a distal end of the suture bridge has a concave shape.

3. The surgical fixation assembly of claim 1, wherein the at least one rib is two ribs.

4. The surgical fixation assembly of claim 3, wherein the suture bridge is connected to and extends between the two ribs.

5. The surgical fixation assembly of claim 1, wherein the first transfer loop is configured to pull an end of the first repair leg through the first constriction element to form a first reducible loop.

6. The surgical fixation assembly of claim 5, wherein the first constriction element is configured to allow the first reducible loop to be tightened but not loosened.

7. The surgical fixation assembly of claim 1, wherein the second transfer loop is configured to pull an end of the second repair leg through the second constriction element to form a second reducible loop.

8. The surgical fixation assembly of claim 7, wherein the second constriction element is configured to allow the second reducible loop to be tightened but not loosened.

9. The surgical fixation assembly of claim 1, wherein the suture construct is coupled to the suture bridge by a coupling region of the repair leg, the coupling region extending between the first repair leg and the second repair leg.

10. The surgical fixation assembly of claim 9, wherein the first constriction element is adjacent the coupling region.

11. The surgical fixation assembly of claim 9, wherein the second constriction element is adjacent the coupling region.

12. The surgical fixation assembly of claim 9, wherein the coupling region is attached to the suture bridge by one of a luggage tag coupling or a knot.

13. The surgical fixation assembly of claim 1, wherein the anchor is disposed on a distal end of a delivery device such that the first and second repair legs and the first and second transfer sutures extend through a cannulation of the delivery device.

14. The surgical fixation assembly of claim 13, wherein the suture bridge is housed within a slot and the at least one rib is housed within at least one corresponding groove of the delivery device.

15. A method of tissue repair comprising:

inserting an anchor of a surgical fixation assembly into a first tissue, the surgical fixation assembly comprising:

the anchor comprising:

a proximal end, a distal end, and threads extending in an open helical form from the proximal to the distal end;

at least one rib extending through an interior of the anchor; and a suture bridge extending at least partially through the interior of the anchor; and a suture construct comprising:

a repair suture having a first repair leg and a second repair leg;

a first transfer suture coupled to the first repair leg via a first constriction element, a first end of the first transfer suture comprising a first free end and a second end of the first transfer suture comprising a first transfer loop; and a second transfer suture coupled to the second repair leg via a second constriction element, a first end of the second transfer suture comprising a second free end and a second end of the second transfer suture comprising a second transfer loop;

passing the first repair leg around or through a second tissue and through the first transfer loop; and using the first free end of the first transfer suture, pulling the first repair leg through the first constriction element to form a first reducible loop around or through the second tissue;

wherein the first constriction element is configured to allow the first reducible loop to be tightened but not loosened around or through the second tissue.

16. The method of claim 15, further comprising:

passing the second repair leg around or through a third tissue and through the second transfer loop; and using the first free end of the second transfer suture, pulling the second repair leg through the second constriction element to form a second reducible loop around or through the third tissue;

wherein the second constriction element is configured to allow the second reducible loop to be tightened but not loosened around or through the third tissue.

17. The method of claim 15, further comprising:

inserting the anchor into the first tissue with a delivery device, the anchor disposed on a distal end of the delivery device such that the first and second repair legs and the first and second transfer sutures extend through a cannulation of the delivery device.

18. The method of claim 15, further comprising:

attaching a coupling region of the repair leg to the suture bridge, the coupling region extending between the first repair leg and the second repair leg.

19. The method of claim 15, wherein the first tissue is bone.

20. The method of claim 15, wherein the second tissue is a soft tissue graft.

* * * * *